United States Patent
Sitton et al.

(10) Patent No.: US 10,619,189 B2
(45) Date of Patent: Apr. 14, 2020

(54) COMPOSITION FOR REDUCING INHIBITION OF NUCLEIC ACID AMPLIFICATION

(71) Applicant: 3M INNOVATIVE PROPERTIES COMPANY, St. Paul, MN (US)

(72) Inventors: Gregory W. Sitton, Minneapolis, MN (US); Wensheng Xia, Woodbury, MN (US); Tonya D. Bonilla, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 248 days.

(21) Appl. No.: 15/571,885

(22) PCT Filed: May 9, 2016

(86) PCT No.: PCT/US2016/031478
§ 371 (c)(1),
(2) Date: Nov. 6, 2017

(87) PCT Pub. No.: WO2016/183012
PCT Pub. Date: Nov. 17, 2016

(65) Prior Publication Data
US 2018/0142280 A1 May 24, 2018

Related U.S. Application Data

(60) Provisional application No. 62/189,991, filed on Jul. 8, 2015, provisional application No. 62/159,733, filed on May 11, 2015.

(51) Int. Cl.
*C12Q 1/68* (2018.01)
*C12Q 1/6806* (2018.01)
*C12Q 1/6844* (2018.01)

(52) U.S. Cl.
CPC ......... *C12Q 1/6806* (2013.01); *C12Q 1/6844* (2013.01); *C12Q 2527/125* (2013.01)

(58) Field of Classification Search
CPC .................................................. C12Q 1/6806

USPC ....................................................... 435/6.12
See application file for complete search history.

(56) References Cited

U.S. PATENT DOCUMENTS

| 7,964,380 B2 | 6/2011 | Utermobhlen et al. |
| 8,288,169 B2 | 10/2012 | Utermohlen et al. |
| 2009/0208919 A1 | 8/2009 | Utermohlen et al. |
| 2012/0003710 A1 | 1/2012 | Leinweber et al. |

FOREIGN PATENT DOCUMENTS

| EP | 0 832 897 | 4/1998 |
| EP | 0 897 978 A2 | 2/1999 |
| EP | 0 897 978 A3 | 2/1999 |
| EP | 0 937 780 | 8/1999 |
| KR | 10-2009-0084364 | 8/2009 |
| WO | WO 2010/004785 | 1/2010 |
| WO | WO 2014/029791 | 2/2014 |

OTHER PUBLICATIONS

Stratagene Catalog p. 39. (Year: 1988).*

* cited by examiner

*Primary Examiner* — Jezia Riley
(74) *Attorney, Agent, or Firm* — Eric E. Silverman

(57) ABSTRACT

A composition for reducing the inhibitory effects of contaminants on nucleic acid amplification is provided. The composition includes a plurality of zirconium oxide particles, a non-ionic surfactant, and an organic iron-chelating reagent. The organic iron-chelating reagent has a first affinity constant greater than or equal to $10^{4.2}$ with respect to ferric iron and a second affinity constant less than $10^{3.8}$ with respect to magnesium, wherein the first affinity constant and the second affinity constant are determined in deionized water at pH 8.45 and 20° C. Optionally, the composition includes polyvinylpyrrolidone. Optionally, the composition comprises water. The composition has a pH of about 8.45 to 8.85. Methods of using the composition to prepare a sample for nucleic acid amplification are also provided.

20 Claims, No Drawings
Specification includes a Sequence Listing.

COMPOSITION FOR REDUCING INHIBITION OF NUCLEIC ACID AMPLIFICATION

CROSS REFERENCE TO RELATED APPLICATIONS

This application is a national stage filing under 35 U.S.C. 371 of PCT/US2016/031478, filed May 9, 2016, which claims the benefit of U.S. Provisional Patent Application Nos. 62/159,733, filed May 11, 2015 and 62/189,991, filed Jul. 8, 2015, the disclosures of which are incorporated by reference in their entirety herein.

This application has associated with it a sequence listing with the file name Sequence_Listing_76042US003.TXT, created Apr. 25, 2016. The sequence listing file contains 1,885 bytes and it is incorporated herein by reference in its entirety.

BACKGROUND

Conventional methods for the detection of pathogens and other microorganisms are based on culture methods, but these are time consuming, laborious, and no longer compatible with the needs of quality control and diagnostic laboratories to provide rapid results.

Efforts to overcome problems like culturing the microorganisms, false positives in pathogen detection have led to the development of genetic testing such as DNA-based diagnostic methods or nucleic acid proliferation methods. The use of DNA-based methods derives from the premise that each species of pathogen carries unique DNA or RNA signature that differentiates it from other organisms. These techniques are the most promising and are increasingly used for rapid, sensitive and specific detection of microbes.

Advances in biotechnology have led to the development of a diverse array of assays for efficient nucleic acid amplification.

The effective genetic testing of samples containing microorganisms/pathogens requires rapid sensitive assay methods that gives instant or real time results. Time and sensitivity of analysis and inhibition of nucleic acid amplification caused by inhibitory substances in the sample are certain limitations related to the usefulness of genetic testing.

It is desirable to have a composition and a method to efficiently and rapidly reduce or eliminate the inhibition of the nucleic acid amplification of the intended target.

SUMMARY

The present disclosure provides a composition for eliminating sample inhibition in a nucleic acid amplification reaction and a nucleic acid amplification method using this composition.

In a first aspect, a composition is provided for eliminating sample inhibition in a nucleic acid amplification reaction, said composition comprising a plurality of zirconium oxide particles, a nonionic surfactant, and an organic iron-chelating reagent. The composition can have a pH of about 8.45 to 8.85. The organic iron-chelating reagent can have a first affinity constant greater than or equal to $10^{4.2}$ with respect to ferric iron and a second affinity constant less than $10^{3.8}$ with respect to magnesium, wherein the first affinity constant and the second affinity constant are determined in 20° C. deionized water at pH 8.45.

In any of the above embodiments, the composition further can comprise water, wherein the surfactant is in the composition at a concentration greater than or equal to 0.005% (mass/volume). In any of the above embodiments, the composition further can comprise ferric iron. In any of the above embodiments, the zirconium oxide particles can have a median particle diameter less than about 1 micron. In any of the above embodiments, the organic iron-chelating reagent can comprise EGTA, wherein a molar ratio of the ferric iron to the EGTA can be about 0.04 to about 0.28. In any of the above embodiments, the composition further can comprise polyvinylpyrrolidone. In any of the above embodiments, the composition further can comprise a nanoparticle dispersion stabilizer.

In a second aspect, the present disclosure provides a nucleic acid amplification method, said method comprising a) contacting a composition comprising a plurality of zirconium oxide particles, a nonionic surfactant, and an organic iron-chelating reagent with a target sample to form an aqueous mixture; wherein the composition has a pH of about 8.45 to 8.85; wherein the surfactant is in the mixture at a concentration greater than or equal to 0.005% (mass/volume); wherein the organic iron-chelating reagent has a first affinity constant greater than or equal to $10^{4.2}$ with respect to ferric iron and a second affinity constant less than $10^{3.8}$ with respect to magnesium, wherein the first affinity constant and the second affinity constant are determined in 20° C. deionized water at pH 8.45; b) subjecting the mixture of step a) to thermal lysis; and c) subsequent to step b), subjecting a portion of the mixture to a nucleic acid amplification process.

In an embodiment, the present disclosure provides an isothermal amplification method, said method comprising a) contacting a composition comprising a plurality of zirconium oxide particles, a nonionic surfactant, and an organic iron-chelating reagent with a target sample to form an aqueous mixture; wherein the composition has a pH of about 8.45 to 8.85; wherein the surfactant is in the mixture at a concentration greater than or equal to 0.005% (mass/volume); wherein the organic iron-chelating reagent has a first affinity constant greater than or equal to $10^{4.2}$ with respect to ferric iron and a second affinity constant less than $10^{3.8}$ with respect to magnesium, wherein the first affinity constant and the second affinity constant are determined in 20° C. deionized water at pH 8.45; b) subjecting the mixture of step a) to thermal lysis; and c) subsequent to step b), subjecting a portion of the mixture to isothermal nucleic acid amplification.

In a third aspect, the present disclosure provides a kit comprising a plurality of zirconium oxide particles, a nonionic surfactant, and an organic iron-chelating reagent. The organic iron-chelating reagent can have a first affinity constant greater than or equal to $10^{4.2}$ with respect to ferric iron and a second affinity constant less than $10^{3.8}$ with respect to magnesium, wherein the first affinity constant and the second affinity constant are determined in 20° C. deionized water at pH 8.45.

In any of the above embodiments, the kit further can comprise ferric iron. In any of the above embodiments of the kit, the ferric iron can be present in the kit as ferric ammonium citrate. In any of the above embodiments of the kit, the zirconium oxide particles can have a median particle diameter less than about 1 micron. In any of the above embodiments of the kit, the organic iron-chelating reagent can comprise EGTA. In any of the above embodiments, the kit further can comprise an effective amount of non-fat milk.

The foregoing has outlined some pertinent objects of the disclosure. These objects should be construed to be merely illustrative of some of the more prominent features and applications of the intended disclosure. The disclosure includes other features and advantages which will be described or will become apparent from the following more detailed description of the embodiment.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. It is to be understood that other embodiments may be utilized and structural or logical changes may be made without departing from the scope of the present disclosure. The present disclosure will now be described more fully herein after. For the purposes of the following detailed description, it is to be understood that the disclosure may assume various alternative variations and step sequences, except where expressly specified to the contrary. Thus, before describing the present disclosure in detail, it is to be understood that this disclosure is not limited to particularly exemplified systems or embodiments that may of course, vary. The use of examples anywhere in this specification including examples of any terms discussed herein is illustrative only, and in no way limits the scope and meaning of the disclosure or of any exemplified term. Likewise, the disclosure is not limited to various embodiments given in this specification.

As used herein, the singular forms "a," "an," and "the" include plural reference unless the context clearly dictates otherwise. The term "and/or" means one or all of the listed elements or a combination of any two or more of the listed elements.

When the term "about" is used in describing a value or an endpoint of a range, the disclosure should be understood to include both the specific value and end-point referred to.

As used herein the terms "comprises", "comprising", "includes", "including", "containing", "characterized by", "having" or any other variation thereof, are intended to cover a non-exclusive inclusion.

As used herein, the phrase "nucleic acid," and "nucleic acid sequence," are interchangeable and not intended to be limiting. "Nucleic acid" shall have the meaning known in the art and refers to DNA (e.g., genomic DNA, cDNA, or plasmid DNA), RNA (e.g., mRNA, tRNA, or rRNA), and PNA. It may be in a wide variety of forms, including, without limitation, double-stranded or single-stranded configurations, circular form, plasmids, relatively short oligonucleotides, peptide nucleic acids also called PNA's and the like. The nucleic acid may be genomic DNA, which can include an entire chromosome or a portion of a chromosome. The DNA may include coding (e.g., for coding mRNA, tRNA, and/or rRNA) and/or noncoding sequences (e.g., centromeres, telomeres, intergenic regions, introns, transposons, and/or microsatellite sequences). The nucleic acid may include any of the naturally occurring nucleotides as well as artificial or chemically modified nucleotides, mutated nucleotides, etc. The nucleic acid can include a non-nucleic acid component, e.g., peptides (as in PNA's), labels (radioactive isotopes or fluorescent markers), and the like.

As used herein, "amplifying" and "amplification" refers to a broad range of techniques for increasing polynucleotide sequences, either linearly or exponentially. Exemplary amplification techniques include, but are not limited to, polymerase chain reaction (PCR) or any other method employing a primer extension step. Other non-limiting examples of amplification include, but are not limited to, ligase detection reaction (LDR) and ligase chain reaction (LCR). Amplification methods may comprise thermal-cycling or may be performed isothermally such as Loop mediated isothermal amplification (LAMP-BART). In various embodiments, the term "amplification product" or "amplified product" includes products from any number of cycles of amplification reactions.

As used herein, the "polymerase chain reaction" or PCR is an amplification of nucleic acid consisting of an initial denaturation step which separates the strands of a double stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon polynucleotide complementary to the target sequence, and (iii) a denaturation step which causes the separation of the amplicon from the target sequence. Each of the above steps may be conducted at a different temperature, preferably using an automated thermocycler.

As used herein, "isothermally amplified" or "isothermal amplification" and like terms refers to a method of amplifying nucleic acid that is conducted at a constant temperature in contrast to amplifications that require cycling between high and low temperatures unlike traditional PCR reactions. This requires that the DNA polymerase is a DNA polymerase having strand displacement activity. Isothermal amplifications are often conducted at substantially a single temperature because primers bind to displaced DNA strands. In isothermal amplifications the reaction mixture comprising the nucleic acid sample and optionally all primers may be heated to a denaturation temperature at which double-stranded nucleic acid in the reaction mixture denatures into single strands (e.g., at least 85° C. to 90° C.) prior to the amplification and optionally prior to addition of the DNA polymerase when the DNA polymerase is inactivated at the denaturation temperature.

As used herein, the terms "intended target", "target nucleic acid region," "target specific nucleic acid," "target region," "target signature sequence" "target nucleic acid(s)", "target nucleic acid sequences," "target" or "target polynucleotide sequence" refers to a nucleic acid of interest.

As used herein, "detecting" or "detection" refers to the disclosure or revelation of the presence or absence in a sample of a target polynucleotide sequence or amplified target polynucleotide sequence product. The detecting can be by end point, real-time, enzymatic, and by resolving the amplification product on a gel and determining whether the expected amplification product is present, or other methods known to one of skill in the art.

As used herein the term "sample" refers to a starting material suspected of containing a nucleic acid. Detecting the nucleic acid in the sample enables one to detect the presence of a microorganism. Examples of samples include, but are not limited to, food samples (including but not limited to samples from food intended for human or animal consumption such as processed foods, raw food material, produce (e.g., fruit and vegetables), legumes, meats (from livestock animals and/or game animals), fish, sea food, nuts, beverages, drinks, fermentation broths, and/or a selectively enriched food matrix comprising any of the above listed foods), water samples, environmental samples (e.g., soil samples, dirt samples, garbage samples, sewage samples, industrial effluent samples, air samples, or water samples from a variety of water bodies such as lakes, rivers, ponds etc.), air samples (from the environment or from a room or a building), clinical samples, samples obtained from humans suspected of having a disease or condition, veterinary samples, forensic samples, agricultural samples, pharmaceutical samples, biopharmaceutical samples, samples from food processing and manufacturing surfaces, and/or biological samples. Examples for nonfood samples as per the present disclosure may be culture broths. "Culture broth" as used herein refers to a liquid medium for culturing the microorganism.

As used herein, an "inhibitor" means any compound, substance, or composition, or combination thereof, that acts to decrease the activity, precision, or accuracy of an assay, either directly or indirectly, with respect to the activity, precision, or accuracy of the assay when the inhibitor is absent. An inhibitor can be a molecule, an atom, or a combination of molecules or atoms without limitation.

In accordance to one aspect of the present disclosure, the term "inhibitors" as used herein refers to inhibitors of enzymes used in amplification reactions, for example. Examples of such inhibitors typically include but not limited to proteins, peptides, lipids, carbohydrates, polyphenols, heme and its degradation products, urea, bile acids, humic acids, polysaccharides, cell membranes, and cytosolic components. The major inhibitors in human blood for PCR are hemoglobin, lactoferrin, and IgG, which are present in erythrocytes, leukocytes, and plasma, respectively. Examples of inhibitors also include iron ions or salts thereof, other metal salts such as alkali metal ions, transition metal ions etc., and indicator dyes present in growth medium.

In an embodiment of the present disclosure, esculin which is an indicator dye may act as inhibitor. Esculin is a coumarin glucoside (6-(beta-D-glucopyranosyloxy)-7-hydroxy-2H-1-benzopyran-2-one, CAS No. 531-75-9) obtained from *Aesculus hippocastanum* (the horsechestnut) and is characterized by its fine blue fluorescent solutions. Esculin is generally added to bacterial culture broths as an indicator; for e.g., in *Listeria* culture. The esculin reaction in demi-Fraser (DF), UVM, and Fraser broth base, (which a *Listeria*-selective enrichment broth bases), is highlighted as a highly likely contributor to assay inhibition. In this reaction esculin

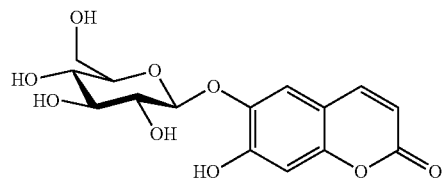

is hydrolyzed by specific bacteria to 6,7 dihydroxycoumarin (aesculetin) and glucose. The aesculetin:

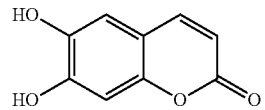

then complexes with ferric ions to form a black complex. Aesculetin is in the coumarin family of drugs and coumarins are known to modify the activity of DNA acting enzymes.

As used herein, the meaning of "surfactant" is the broadest definition that is readily recognized by a person of ordinary skill in the art. That is, surfactants are wetting agents that lower the surface tension of a liquid and/or lower the interfacial tension between two liquids. A surfactant that does not have a positive or negative charge in water, yet is soluble in water, is a "non-ionic surfactant".

As used herein, "nonionic surfactant" refers to a surfactant molecule whose polar group is not electrically charged. Combinations of two or more non-ionic surfactants are encompassed within the term "non-ionic surfactant". In certain embodiments, one or more surfactants may be used.

As used herein, polyvinylpyrrolidone (PVP) is a water-soluble polymer made from the monomer N-vinylpyrrolidone. Polyvinylpolypyrrolidone (PVPP) is a highly cross-linked modification of PVP. As described herein, polyvinylpyrrolidone, or a modification thereof, can be included in an amplification reaction mixture so as to reduce or eliminate inhibitory substances. A modified PVP includes, but is not limited to polyvinylpolypyrrolidone (PVPP), which is an insoluble highly cross-linked modification of PVP. It will be understood that disclosure herein related to PVP can be adapted to PVPP.

In an embodiment, the composition may comprises a non-ionic polymeric fluorochemical surfactant which belongs to a class of coating additives which provide low surface tensions and exhibits good thermal stability when used in thermal processing applications. A non-ionic polymeric fluorochemical surfactant as per certain embodiments of the present disclosure may be FC-4430 which is 3M™ Novec™ fluorosurfactant.

As used herein the terms "ethylene glycol tetraacetic acid" and "EGTA" refer to ethylene glycol-bis(2-aminoethylether)-N,N,N',N'-tetraacetic acid, a chelating agent. EGTA is a colorless solid which has lower affinity for magnesium, making it more selective for calcium ions. EGTA is useful for making buffer solutions to chelate calcium ions when calcium ions are less concentrated than magnesium, as found in living cells. EGTA is also useful in enzyme assays.

As used herein the term "cell lysis" refers to a process of releasing materials in a cell by disrupting the cell membrane, and in particular, a process of extracting intracellular materials from a cell to isolate DNA or RNA before amplification, such as PCR, LAMP BART methods and likewise.

According to an embodiment of the present disclosure, cell lysis may be done by thermal methods. The thermal method may be properly selected by those skilled in the art according to the form of cell sample and characteristics of reaction vessel.

As used herein, the term "microorganism" or "microbe" refers to any microscopic organism, which may be a single cell or multicellular organism. The term is generally used to refer to any prokaryotic or eukaryotic microscopic organism capable of growing and reproducing in a suitable culture medium, including without limitation, one or more of bacteria. Microorganisms encompassed by the scope of the present invention includes prokaryotes, namely the bacteria and archaea; and various forms of eukaryotes, comprising the protozoa, fungi, algae and the like. As used herein, the term "culture" or "growth" of microorganisms refers to the method of multiplying microbial organisms by letting them reproduce in predetermined culture media under conditions conducive for their growth. More particularly it is the method of providing a suitable culture medium and conditions to facilitate at least one cell division of a microorganism. Culture media may be solid, semisolid or liquid media containing all of the nutrients and necessary physical growth parameters necessary for microbial growth. The term "target microorganism" refers any microorganism that is desired to be detected.

As used herein, the term "enrichment" refers to the culture method of selectively enriching the growth of a specific microorganism by providing medium and conditions with specific and known attributes that favors the growth of that particular microorganism. The enrichment culture's environment will support the growth of a selected microorganism, while inhibiting the growth of others.

The use of conventional DNA-based methods is to some extent restricted by the presence of inhibitors. The occurrence of such so called inhibitors, which comprises all substances that have a negative effect on the nucleic acid proliferation reactions, is one of the drawbacks of genetic testing. These inhibitors can originate from the sample itself or may be introduced during sample processing or nucleic acid extraction. The consequence of a partly or total inhibition of the nucleic acid proliferation reactions is a decreased sensitivity or false-negative results, respectively.

Despite the availability of numerous genetic based methods, there is no single rapid, sensitive, inexpensive and less laborious method to efficiently and rapidly reduce or eliminate the inhibition of the nucleic acid amplification of the intended target. To quickly determine the presence of pathogen in targeted sample, there is a need to develop a reliable and accurate assay method which can cater to the increasing need of finding faster, accurate and less time consuming and less laborious assay techniques.

In competitive PCR systems a challenge to ease of use is the inclusion of a protease step. This protease step is used for reducing sample inhibition by digesting food protein (especially red meats) as well as lysing cells. Surprisingly, it has been found that a composition and a method as per the present disclosure eliminates the need for proteasing a sample by using zirconium oxide particles in combination with an organic iron-chelating reagent to neutralize inhibitory proteins. Advantageously the present disclosure eliminates the step of isolation/purification which makes the current assay method faster and simpler.

The present disclosure describes the composition and method of nucleic acid amplification which eliminates the need to protease or otherwise reduces background protein from the sample. This in turn also leads to the elimination of one of the assay steps of the conventional nucleic acid amplification methods.

The present disclosure generally relates to novel compositions and methods for nucleic acid proliferation of a sample which comprises a cell lysis step and nucleic acid amplification step without an isolation/purification step such as chromatography, centrifugation and likewise in between.

A composition or a method of the present disclosure can be used to detect a variety of microorganisms that are found in food or beverage materials (e.g., ingredients, in-process compositions, and finished goods). The compositions and methods can be particularly useful for detecting relatively low numbers of pathogenic microorganisms in the food or beverage materials.

Non-limiting examples of pathogenic microorganisms that can be detecting using compositions and methods of the present disclosure include a *Salmonella* species (e.g., *Salmonella enteritidis, Salmonella typhimurium*), a *Clostridium* species (e.g., *Clostridium perfringens, Clostridium botulinum*), *Bacillus cereus*, a *Campylobacter* species (e.g., *Campylobacter jejuni*), a *Staphylococcus* species (e.g., *Staphylococcus aureus*), *Escherichia coli* (e.g., *E. coli* O157:H7), a *Listeria* species (e.g., *Listeria monocytogenes*), a *Vibrio* species (e.g., *Vibrio cholerae, Vibrio parahaemolyticus*), and a *Yersinia* species (e.g., *Yersinia enterocolitica, Yersinia pseudotuberculosis*).

A composition of the present disclosure is typically used as an aqueous solution comprising the respective chemical components. Thus, in any embodiment, a composition of the present disclosure comprises water. A predetermined volume of the aqueous composition can be mixed with a predetermined amount (e.g., volume) of a sample to form a mixture that is treated (e.g., by heating) to lyse any microorganisms, if present, in the sample. A portion of the resulting lysate can be used in a nucleic amplification process to detect nucleic acid sequences that indicate a presence of one or more target microorganisms in the original sample.

Typically, the sample (e.g., ground beef, a carcass rinse, process water, residue from an environmental (e.g., food-processing equipment) swab or sponge) is suspended in an aqueous liquid (e.g., water or a buffer). Thus, a first predetermined volume of the aqueous sample is mixed with a second predetermined volume of an aqueous solution comprising the composition of the present disclosure to form the mixture that is subjected to a lysis treatment. Accordingly, each component of the composition of the present disclosure is present in the aqueous composition at a concentration that takes into account the dilution that occurs when the sample is mixed with the composition.

According to the present disclosure, the ratio of the first predetermined volume to the volume of the mixture formed by mixing the first and second predetermined volumes is less than or equal to 1:10. In any embodiment, the ratio of the first predetermined volume to the volume of the mixture formed by mixing the first and second predetermined volumes is about 1:10 to about 1:300. In any embodiment, the ratio of the first predetermined volume to the volume of the mixture formed by mixing the first and second predetermined volumes is about 1:10, about 1:20, about 1:25, about 1:30, about 1:40, about 1:50, about 1:100, about 1:200, about 1:250, or about 1:300.

Accordingly, the present disclosure provides a composition (e.g., an aqueous liquid composition) comprising a plurality of zirconium oxide particles, an organic iron-chelating reagent, and a non-ionic surfactant at a concentration greater than or equal to 0.005% (mass/volume). The composition has a pH of about 8.45-8.85. The composition can be used in nucleic acid amplification methods to reduce and/or eliminate sample inhibition of the nucleic acid amplification reaction. Optionally, the composition can comprise ferric ions and/or polyvinylpyrrolidone as described herein.

In any embodiment, a suitable pH for the composition is at least 8.45. In any embodiment the pH may be within the range of 8.45 to 8.85. In certain embodiments, a pH of 8.65 to 8.75 may be used. In other embodiments, a pH of 8.75, to 8.85 may be used.

In any embodiment, the zirconium oxide particles may comprise nanoparticles (e.g., the zirconium oxide particles have a median particle size that is about 100 nm to less than 1.0 µm). In any embodiment, the zirconium oxide particles can have a mean particle size of about 100 nm to about 200 nm. In any embodiment, the zirconium oxide particles can have a mean particle size of about 100 nm to about 250 nm. In any embodiment, the zirconium oxide particles can have a mean particle size of about 100 nm to about 500 nm. These particles can exist in a stable dispersion at the pH indicated above by the addition of the stabilizer citrate.

A dispersion of zirconium oxide nanoparticles may be characterized by its surface area per unit volume. In any embodiment, a composition of the present disclosure may comprise nanoparticles having a surface area of at least 10 $m^2/L$. In any embodiment, a composition of the present disclosure may comprise nanoparticles having a surface area of about 10 $m^2/L$ to about 600 $m^2/L$, inclusive. In any embodiment, a composition of the present disclosure may comprise nanoparticles having a surface area of at least about 25 $m^2/L$ to about 600 $m^2/L$. In any embodiment, a composition of the present disclosure may comprise nanoparticles having a surface area of at least about 50 $m^2/L$ to about 600 $m^2/L$. In any embodiment, a composition of the present disclosure may comprise nanoparticles having a surface area of at least about 100 $m^2/L$ to about 600 $m^2/L$. In any embodiment, a composition of the present disclosure may comprise nanoparticles having a surface area of at least about 200 $m^2/L$ to about 600 $m^2/L$. In any embodiment, a composition of the present disclosure may comprise nanoparticles having a surface area of at least about 300 $m^2/L$ to about 600 $m^2/L$. In any embodiment, a composition of the present disclosure may comprise nanoparticles having a surface area of at least about 400 $m^2/L$ to about 600 $m^2/L$. In any embodiment, a composition of the present disclosure may comprise nanoparticles having a surface area of about 600 $m^2/L$.

The compositions of the present disclosure comprising $ZrO_2$ nanoparticles can be stabilized such that the particles substantially remain in suspension for extended periods of time (e.g., months, and/or years) and/or are resuspended with minimal effort. This can be accomplished by adding a dispersion stabilizer to the composition. A particularly-preferred dispersion stabilizer that can be used in a composition of the present disclosure includes a polycarboxylic acid compound such as 2-hydroxypropane-1,2,3-tricarboxylic acid (citric acid) or salts thereof, such as potassium citrate, ferric ammonium citrate, for example.

The organic iron-chelating reagent has a predefined affinity constant for ferric ($Fe^{-3}$) iron ions. In deionized water at pH 8.45 and 20° C., the organic iron-chelating reagent has an affinity constant greater than or equal to $10^{4.2}$ with respect to ferric iron ions. The organic iron-chelating reagent also has a predefined affinity constant for magnesium ($Mg^{+2}$) ions. In deionized water at pH 8.45 and 20° C., the organic iron-chelating reagent has an affinity constant less than $10^{3.8}$ with respect to magnesium ions. Thus, in the aqueous composition of the present disclosure at pH 8.45, the organic iron-chelating reagent has a higher affinity for ferric iron ions than for magnesium ions.

Suitable organic iron-chelating reagents include organic molecules. In any embodiment, the organic iron-chelating reagent is water-soluble. In any embodiment, the organic iron-chelating reagent comprises a plurality of carboxylate groups. Non-limiting examples of suitable organic iron-chelating reagents include ethylene glycol-bis(2-aminoethylether)-N,N,N',N'-tetraacetic acid (EGTA); N,N,N',N'-tetrakis(2-pyridylmethyl)ethane-1,2-diamine (TPEN); 1,2-bis(o-aminophenoxy)ethane-N,N,N',N'-tetraacetic acid (BAPTA); N-(2-hydroxyethyl) ethylenediamine-N,N',N'-triacetic acid (HEDTA); and salts thereof.

In any embodiment, the composition optionally comprises ferric iron. Accordingly, an aqueous composition of the present disclosure may comprise ferric iron ions. In any embodiment, the ferric iron can be provided in the composition by ferric ammonium citrate. Thus, the composition may further comprise citrate ions. Advantageously, the citrate ions may facilitate and/or stabilize dispersion of zirconium oxide particles in aqueous compositions of the present disclosure.

In any embodiment, ferric iron can be present in an aqueous liquid composition according to the present disclosure at a concentration of ferric ions (i.e., dissolved ferric iron) of about 55 µM-385 µM. In certain embodiments the concentration of ferric ions may be at least 110 µM, in certain other embodiments it may be at least 165 µM. In other embodiments the concentration of ferric ions may be at least 220 µM, and in other embodiments it may be at least 275 µM or at least 330 µM. According to the present disclosure, in an aqueous wherein the organic iron-chelating reagent comprises EGTA, the composition has a molar ratio of dissolved ferric iron/EGTA of about 0.04 to about 0.28. In certain preferred embodiments, the aqueous composition has a molar ratio of dissolved ferric iron/EGTA of about 0.14 to about 0.18.

In any embodiment of a liquid (e.g., an aqueous liquid) composition according to the present disclosure, ferric iron (provided as ferric ammonium citrate) is present to yield (when the composition is mixed with a sample) a concentration of ferric ions of about 50 µM-350 µM. In certain embodiments the concentration of ferric ions may be at least 100 µM, in certain other embodiments it may be at least 150 µM. In other embodiments the concentration of ferric ions may be at least 200 µM, and in other embodiments it may be at least 250 µM or at least 300 µM. According to the present disclosure, in an aqueous wherein the organic iron-chelating reagent comprises EGTA, the composition has a molar ratio of $Fe^{3+}$/EGTA of about 0.04 to about 0.28. In certain preferred embodiments, the composition has a molar ratio of $Fe^{3+}$/EGTA of about 0.14 to about 0.18.

In an embodiment, the composition of present disclosure comprises at least one non-ionic surfactant. Accordingly, the composition may comprise one or more of any non-ionic surfactant. Preferably, the non-ionic surfactant has a Hydrophilic-lipophilic balance of about 11 to about 16. Surfactants with a Hydrophilic-lipophilic balance in this range permit sufficient activity of the DNA polymerases in PCR and LAMP nucleic acid amplification reactions as well as permit sufficient luciferase and ATP sulphurlyase activity in the BART reporter technology. Examples of suitable non-ionic surfactants include, but are not limited to TRITON™ series of detergents, including, but not necessarily limited to, TRITON X-100 (t-octylphenoxypolyethoxyethanol) and its derivatives, TRITON X-114, TRITON X-405, TRITON X-101, TRITON N-42, TRITON N-57, TRITON N-60, TRITON X-15, TRITON X-35, TRITON X-45, TRITON X-102, TRITON X-155, TRITON X-165, TRITON X-207, TRITON X-305, TRITON X-705-70 and TRITON B-1956; sorbitan fatty acid ester, Polyoxyethylene (POE)sorbitan fatty acid ester (e.g., Tween), POE alkyl ether (e.g., Brij), nonylphenol, lauryl alcohol, polyethylene glycol, polyoxyethylene.polyoxypropylene block polymer, POE alkyl amine, and POE fatty acid bisphenyl ether and fluorosurfactants such as 3M Novec™ engineered liquid surfactants FC-4430 and FC4432, and Dow chemical FS series fluorosurfactants, for example.

In any embodiment of a liquid (e.g., an aqueous liquid) composition according to the present disclosure, the concentration of such a surfactant in the composition is not particularly limited, as long as the beneficial effects of the present invention (i.e., with respect to facilitation of nucleic acid amplification) can be achieved. In any embodiment, a composition of the present disclosure comprises about 0.005% (w/v) to about 0.3% (w/v) surfactant. Accordingly, in any embodiment, a composition of the present disclosure comprises up to about 0.3% (w/v) surfactant. In certain embodiments the concentration of surfactant may be at least 0.01% (w/v) and in certain other embodiments it may be at least 0.025% (w/v) and in another embodiment it is 0.032% (w/v).

Optionally, in any embodiment of the present disclosure, PVP with a nominal molecular weight of 30 KDa to 1.3 MDa may be used. In one aspect of the disclosure, PVP has a nominal molecular weight is 360 KDa.

In an embodiment of the present disclosure, PVP may be included in the composition when low amounts of the surfactant is used. In an embodiment of a liquid (e.g., an aqueous liquid) composition according to the present disclosure, the composition (before adding the sample) may comprise 0% w/v up to about 0.0473% w/v PVP. When the nonionic surfactant is present in the composition at a concentration of 0.0055% to 0.011% w/v, the composition may comprise about 0.011% w/v to about 0.0473% w/v PVP. Each of the above concentrations apply also to a modified PVP.

In an embodiment of the present disclosure, PVP may be included in the composition when low amounts of the surfactant is used. In an embodiment of a liquid (e.g., an aqueous liquid) composition according to the present disclosure, the composition (after adding the sample) may comprise 0% w/v up to about 0.043% w/v PVP. When the nonionic surfactant is present in the composition at a concentration of 0.005% to 0.01% w/v, the composition may comprise about 0.01% w/v to about 0.043% w/v PVP. Each of the above concentrations apply also to a modified PVP.

In certain embodiments of the disclosure (e.g., when the nonionic surfactant concentration is >0.01% w/v), PVP may not be included in the composition.

In any embodiment of the present disclosure, the organic iron-chelating reagent comprises EGTA. In any embodiment, the organic iron-chelating reagent can be provided to the composition in the form of a salt. In certain embodiments, the composition may include, for example, a sodium salt of EGTA. In another embodiment of the present disclosure, the composition may include, for example, a potassium salt of EGTA.

A composition according to the present disclosure may comprise $Fe^{3+}$ (e.g., provided via ferric ammonium citrate) and ethylene glycol tetraacetic acid (e.g., provided via a salt (e.g., a monovalent cation salt) of ethylene glycol tetraacetic acid). Thus, in the composition, there can exist a molar ratio of ethylene glycol tetraacetic acid and $Fe^{3+}$. In any embodiment, the molar ratio of ethylene glycol tetraacetic acid to $Fe^{3+}$ is about 0.04 to about 0.28.

In any embodiment of a liquid (e.g., an aqueous liquid) composition according to the present disclosure, the EGTA may be present at a concentration of 0.5 mM to 5 mM.

In any embodiment, a composition according to the present disclosure optionally comprises an effective amount of a predetermined source of protein (e.g., nonfat milk). The protein in the source can advantageously remove or otherwise bind substances (e.g., polyphenols or other substances, for example found in spices or other foods) that otherwise would interfere with a nucleic acid amplification process.

In any embodiment, a composition according to the present disclosure optionally can comprise magnesium or salts thereof and/or potassium or salts thereof. Accordingly, an aqueous composition according to the present disclosure optionally can comprise magnesium or potassium ions. These may be present in the composition to facilitate the nucleic acid amplification reaction (e.g., PCR (e.g., qPCR), LAMP) that follows the sample preparation step. In any embodiment, an aqueous composition according to the present disclosure can comprise about 1 mM to about 15 mM magnesium ions and/or about 5 mM to about 500 mM potassium ions. In any embodiment, the aqueous composition can comprise about 20 mM to about 60 mM potassium ions.

According to one embodiment of the present disclosure, a sample may be tested directly, or may be prepared or processed in some manner prior to testing. For example, a sample may be processed to enrich any contaminating microbe and may be further processed to separate and/or lyse microbial cells/viral cells/fungal cells contained therein. Lysed microbial cells from a sample may be additionally processed or prepares to separate and/or extract genetic material from the microbe for analysis to detect and/or identify the contaminating microbe. Some embodiments refer to "a nucleic acid in a sample" or a "sample derived nucleic acid" and refer to a nucleic acid comprised in a sample or obtained from a sample. Such nucleic acids can be tested by methods and using compositions described herein.

In certain embodiments of the present disclosure, a sample may be subjected to separation to initially separate microbes of interest from other microbes and other sample components. For example, for complex food samples with complex components separation methods can be used to separate microorganisms from food. Separated microbes from samples may also be enriched prior to analysis. Analysis of a sample may include one or more molecular methods. For example, according to some exemplary embodiments of the present disclosure, a sample may be subject to nucleic acid amplification (for example by LAMP-BART) using appropriate oligonucleotide primers that are specific to one or more microbe nucleic acid sequences that the sample is suspected of being contaminated with. Amplification products may then be further subject to testing with specific probes (or reporter probes) to allow detection of microbial nucleic acid sequences that have been amplified from the sample. In some embodiments, if a microbial nucleic acid sequence is amplified from a sample, further analysis may be performed on the amplification product to further identify, quantify and analyze the detected microbe (determine parameters such as but not limited to the microbial strain, pathogenicity, quantity etc.).

The present disclosure is generally provides a nucleic acid amplification method, said method comprising a) contacting any composition (e.g., aqueous composition) according to the present disclosure with a target sample to form an aqueous mixture wherein the mixture has a pH of about 8.45 to 8.85; b) subjecting the aqueous mixture of step a) to thermal lysis; and c) subsequent to step b), subjecting a portion of the aqueous mixture to isothermal nucleic acid amplification.

In any embodiment of the present disclosure, a nucleic acid amplification method, comprises a) contacting any composition (e.g., aqueous composition) according to the present disclosure with a target sample to form an aqueous mixture wherein the aqueous mixture has a pH of about 8.45 to 8.85; b) subjecting the aqueous mixture of step a) to thermal lysis; and c) subsequent to step b), subjecting the aqueous mixture to isothermal nucleic acid amplification, wherein said method eliminates the inhibition of nucleic acid amplification caused by interfering components present in the sample.

The amplification methods used in a method according to the present disclosure may be performed isothermally. Isothermal techniques include but not limited loop-mediated isothermal amplification (LAMP), strand displacement amplification (SDA), nucleic acid sequence-based amplification (NASBA). The reaction proceeds at a constant temperature using strand displacement reactions. Amplification can be completed in a single step, by incubating the mixture of samples, primers, DNA polymerase with strand displacement activity, and substrates at a constant temperature. In addition to steps or reactions that increase the number of copies of a target nucleic acid sequence, the amplification methods further may include steps or reactions to detect the amplified target nucleic acid sequence. Such detection steps or reactions are well known to a person having ordinary skill in the art and include, for example, bioluminescent real-time reporter (BART) steps or reactions.

In an embodiment of the present disclosure, the isothermal amplification reaction is a Loop-mediated isothermal amplification (LAMP-BART) method. LAMP can amplify DNA with high specificity, efficiency and rapidity under isothermal condition. The LAMP method requires a Bst DNA polymerase and set of four to six specific designed primers that recognize a total of six distinct sequences of the target DNA and with strand displacement activity. In Loop-mediated isothermal amplification (LAMP), target-specific amplification is achieved by the use of 4 to 6 different primers specifically designed to recognize 6 to 8 distinct regions on the target gene, respectively. Such methods typically amplify nucleic acid copies $10^9$-$10^{10}$ times in 15-60 minutes. In addition, the presence of, for example, ATP-sulfurylase, adenosine-5'-O-persulfate, luciferin, and luciferase in the amplification reaction permits detection of a LAMP-mediated amplification reaction via bioluminescence (i.e., the BART reaction).

In addition to the primers, LAMP-BART techniques use Tris, sulphate compounds (such as $MgSO_4$, $NH_4SO_4$) and potassium chloride to maintain enzyme functionality. Thus, such compounds are act as enhancers to facilitate the LAMP-BART coupled reaction. Tris is an organic compound (more formally known as tris (hydroxymethyl) aminomethane, with the formula $(HOCH_2)_3CNH_2$). Strand displacement techniques, such as LAMP, use Tris as a buffer, which maintain the reaction at the optimal pH.

Compositions of the present disclosure optionally can comprise an indicator dye to monitor the approximate temperature of an aqueous solution comprising the composition. Advantageously, the indicator dye can provide a first visual indication (e.g., a first observable color) to indicate that an aqueous mixture comprising the composition has reached a temperature (e.g., about 100° C.) approximately in a range that is suitable for thermal lysis of microbial cells in contact with the composition In addition, the indicator dye can provide a second visual indication (e.g., a second color) to indicate that the aqueous mixture comprising the composition has cooled to a temperature (e.g., ≤° C.) that is suitable to remove a portion of the mixture and place it into a nucleic acid amplification reaction. Certain pH indicators (e.g., those having a transition range that at least partially extends between a pH of about 8.8 and about 7.2) can be readily monitored as the pH of the aqueous mixture changes during heating and cooling steps.

Suitable visible dyes include, for example, Cresol Red, which has a reddish-purple color when pH is higher than 8.8 and a yellow color when pH is less than 7.2

In any of the embodiments of the present disclosure, the indicator dye may be cresol red.

Using LAMP, the target nucleic acid sequence is amplified at a constant temperature of 60° C. to 65° C. using either two or three pairs of primers and a polymerase with high strand displacement activity in addition to a replication activity. The loop-mediated isothermal amplification (LAMP) reaction is a highly specific, sensitive, isothermal nucleic acid amplification reaction. LAMP employs a primer set of four essential primers, termed forward inner primer (FIP), backward inner primer (BIP), forward displacement primer (F3) and backward displacement primer (B3). These four different primers are used to identify 6 distinct regions on the target gene, which adds highly to the specificity. Due to the specific nature of the action of these primers, the amount of DNA produced in LAMP is considerably higher than PCR-based amplification. Furthermore, two optional primers can be included which effectively accelerate the reaction; these are termed forward loop primer (LF) and backward loop primer (LB). The inner primers (FIP and BIP) contain sequences of the sense and antisense strands of the target DNA, while the displacement primers (F3 and B3) and the loop primers (LF and LB) each contain a single target sequence. In total, eight target sequences are recognized when including loop primers (LF and LB) in the reaction. A DNA polymerase is used to amplify the target sequence of interest. Many different DNA polymerases may be used including engineered DNA polymerases not found in nature, the most common being the Bst DNA polymerase while the Geobacillus sp. large fragment (GspSSD) DNA polymerase is used less often.

The LAMP reaction is initiated by DNA synthesis primed by the inner primers (FIP and BIP). This is followed by DNA synthesis primed by a displacement primer (F3 or B3) which releases a single-stranded DNA. This single-stranded DNA serves as template for DNA synthesis primed by the second inner and displacement primers that hybridize to the other end of the target. This produces a stem-loop DNA structure. In subsequent LAMP cycling, one inner primer hybridizes to the loop on the product and initiates displacement DNA synthesis. This yields the original stem-loop DNA and a new stem-loop DNA with a stem twice as long. The cycling reaction continues with accumulation of around $10^9$ copies of target in less than an hour. The inclusion of one or two loop primers (LF and/or LB) accelerates the LAMP reaction by hybridizing to the stem-loops, except for the loops that are hybridized by the inner primers, and prime strand displacement DNA synthesis. A variety of LAMP amplification detection methods exist. Non-specific target detection may be obtained through visual identification of a turbid sample as magnesium pyrophosphate precipitates in a positive LAMP reaction. For better visibility of a positive reaction, various agents, such as hydroxy naphthol blue or calcein, may be added to the reaction. Alternatively, fluorescent detection may be achieved using a DNA intercalating dye, such as cresol red, SYBR green, Picogreen or propidium iodide, which is added to the reaction reagent or added after the completion of the reaction for end point analysis.

In an embodiment, the present disclosure provides a method that includes contacting a sample suspended in the composition as per the present disclosure with components of an isothermal nucleic acid amplification reaction for a target nucleic acid species, thereby providing an amplification reaction mixture; incubating the amplification reaction mixture under conditions sufficient for the isothermal nucleic acid amplification reaction to proceed, thereby providing a product; and determining whether an indicator of the target nucleic acid species is present in the product.

In another embodiment, the disclosure features a method that includes performing an isothermal reaction of an amplification reaction mixture to provide a product, the mixture comprising a lysate which includes the sample mixed with the composition as per the present disclosure and components of a nucleic acid amplification reaction for a target nucleic acid species; and determining whether an indicator of the target nucleic acid species is present in the product.

In any embodiment of the method disclosed herein, subjecting a portion of the aqueous mixture to a nucleic acid amplification process comprises amplifying a target polynucleotide associated with a pathogenic microorganism. Non-limiting examples of pathogenic microorganisms that can be detecting by the method include a pathogenic microorganism selected from the group consisting of a *Salmonella* species, a *Clostridium* species, *Bacillus cereus*, a *Campylobacter* species, a *Staphylococcus* species, *Escherichia coli*, a *Listeria* species, a *Vibrio* species, and a *Yersinia* species.

The components of an isothermal amplification reaction may be provided in a solution and/or in dried (e.g., lyophilized) form. When one or more of the components are provided in dried form, a resuspension or reconstitution buffer may be also be used. Alternatively, after forming an aqueous mixture comprising the sample and the composition of the present disclosure and, after subjecting the aqueous mixture to a thermal lysis procedure, the aqueous mixture can be used to reconstitute the components of the isothermal reaction.

Based on the particular type of amplification reaction, the reaction mixture can contain buffers, salts, nucleotides, and other components as necessary for the reaction to proceed. The reaction mixture may be incubated at a specific temperature appropriate to the reaction.

The target nucleic acid may be a nucleic acid present in an animal (e.g., human), plant, fungal (e.g., yeast), protozoan, bacterial, or viral species. For example, the target nucleic acid may be present in the genome of an organism of interest (e.g., on a chromosome) or on an extra-chromosomal nucleic acid. In some embodiments, the target nucleic acid is an RNA, e.g., an mRNA. In particular embodiments, the target nucleic acid is specific for the organism of interest, i.e., the target nucleic acid is not found in other organisms or not found in organisms similar to the organism of interest.

The present disclosure has manifold applications in various fields that require method of detecting a microorganism in a sample wherein the composition may be used as a suspending medium into which sample is held during a thermal lysis step and composition may be used as the aqueous medium in which a lyophilized pellet of LAMP-BART nucleic acid amplification reagents are dissolved and allowed to react.

The present disclosure effortlessly allows the user to merely contact the sample with the composition comprising a plurality of zirconium oxide particles as described herein, an organic iron-chelating reagent, and a non-ionic surfactant, optionally ferric iron, and optionally polyvinylpyrrolidone at a pH of about 8.4 to 8.85 to form an aqueous mixture; subsequently to subject the aqueous mixture to a lysis procedure (e.g., a thermal lysis procedure); and, after cooling the aqueous mixture, to subject the aqueous mixture to a nucleic acid amplification reaction (e.g., an isothermal nucleic acid amplification reaction or a thermocycling nucleic acid amplification reaction) for detection of microorganisms.

In another embodiment, the present disclosure provides kits. In general, the kit comprises a plurality of zirconium oxide particles (e.g., nanoparticles) as described herein, an organic iron-chelating reagent according to the present disclosure, a non-ionic surfactant, optionally ferric iron, and optionally polyvinylpyrrolidone.

In an embodiment, the kit comprises a plurality of zirconium oxide particles as described herein, an organic iron-chelating reagent, and a non-ionic surfactant. The organic iron-chelating reagent has a first affinity constant greater than or equal to $10^{4.2}$ with respect to ferric iron and a second affinity constant less than $10^{3.8}$ with respect to magnesium, wherein the first affinity constant and the second affinity constant are determined in deionized water at pH 8.45 and 20° C.

In any embodiment of the kit, the organic iron-chelating reagent can comprise a plurality of carboxylate groups. In any of the above embodiments, the kit further can comprise 2-hydroxypropane-1,2,3-tricarboxylic acid (citric acid), or a salt thereof such as a sodium or potassium salt. In any of the above embodiments of the kit, the organic iron-chelating reagent can comprise EGTA, wherein a molar ratio of the ferric iron to the EGTA is about 0.04 to about 0.28.

In another embodiment, a kit may further comprise a component selected from the group consisting of fluorosurfactant, indicator dye, preservative, buffering agents and enhancers of LAMP-BART reaction and combinations thereof. In any embodiment of the kit, any one or more of the foregoing components may be present in the kit in the composition. The kit may comprise at least one primer, such as two primers, for amplification of a target nucleic acid. It also may include at least one other primer for amplification of a target nucleic acid, which can be, but is not necessarily, the same nucleic acid (and even the same sequence within the same nucleic acid) that is the target for one or more other primer(s) in the kit. In some embodiments, the kits comprise two or more primers for amplifying one or more unique genomic sequences.

In another embodiment, the kits comprise the components (i.e., the composition, the components thereof, the fluorosurfactant, the indicator dye, the preservative, the buffering agent and/or the enhancer of the LAMP-BART reaction) in a single package or in more than one package within the same kit. Where more than one package is included within a kit, each package can independently contain a single component or multiple components, in any suitable combination. As used herein, a combination of two or more packages or containers in a single kit is referred to as "in packaged combination".

In any embodiment of the kit, any one or more of the plurality of zirconium particles, the organic iron-chelating reagent, the ferric iron, the polyvinylpyrrolidone, the nonionic surfactant, the fluorosurfactant, the indicator dye, the preservative, the buffering agent, or enhancer is disposed in an aqueous solution. In any embodiment, the aqueous solution can have a pH of about 8.45 to 8.85.

The kits and containers within the kits may be fabricated with any known material. For example, the kits themselves may be made of a plastic material or cardboard. The containers that hold the components may be, for example, a plastic material or glass. Different containers within one kit may be made of different materials. In embodiments, the kit can contain another kit within it.

The kit of the present disclosure may comprise one or more components useful for amplifying target sequences. In embodiments, some or all of the reagents and supplies necessary for performing LAMP-BART method are included in the kit. Non-limiting examples of reagents are buffers (e.g., a buffer containing Tris, HEPES, and the like), salts, and a template-dependent nucleic acid extending enzyme (such as a thermostable enzyme, such as Taq polymerase), a buffer suitable for activity of the enzyme, and additional reagents needed by the enzyme, such as dNTPs, dUTP, and/or a UDG enzyme. In embodiments, the kit comprises enhancers such as potassium chloride and ammonium sulphate to facilitate the enzymatic reactions. A non-limiting example of supplies is reaction vessels (e.g., microfuge tubes).

In any embodiment, a kit of the present disclosure further comprises a reagent (e.g., a primer) for amplifying a target polynucleotide. In any embodiment, the target polynucleotide is associated (e.g., specifically associated) with a pathogenic microorganism. In any embodiment, the pathogenic microorganisms is selected from the group consisting of a *Salmonella* species, a *Clostridium* species, *Bacillus cereus*, a *Campylobacter* species, a *Staphylococcus* species, *Escherichia coli*, a *Listeria* species, a *Vibrio* species, and a *Yersinia* species.

The kit has the advantages of high sensitivity, high specificity, ease of operation, capability of judging a result through naked eyes and the like.

Exemplary Embodiments

Embodiment A is a composition, said composition comprising a plurality of zirconium oxide particles, a non-ionic surfactant, and an organic iron-chelating reagent, wherein the composition has a pH of about 8.45 to 8.85, wherein the organic iron-chelating reagent has a first affinity constant greater than or equal to $10^{4.2}$ with respect to ferric iron and a second affinity constant less than $10^{3.8}$ with respect to magnesium, wherein the first affinity constant and the second affinity constant are determined in deionized water at pH 8.45 and 20° C.

Embodiment B is the composition of Embodiment A, further comprising water, wherein the nonionic surfactant s present in the composition at a concentration greater than or equal to 0.005% (mass/volume).

Embodiment C is the composition of Embodiment A or Embodiment B, wherein the plurality of particles has a mean particle size that is less than about 1 μm.

Embodiment D is the composition of any one of Embodiments A through C, wherein the plurality of zirconium oxide particles has a surface area of about 10 $m^2/L$ to about 600 $m^2/L$.

Embodiment E is the composition of any one of the preceding Embodiments, wherein the organic iron-chelating reagent comprises a plurality of carboxylate groups.

Embodiment F is the composition of any one of the preceding Embodiments, wherein the organic iron-chelating reagent is selected from the group consisting of ethylene glycol-bis(2-aminoethylether)-N,N,N',N'-tetraacetic acid; N,N,N',N'-tetrakis(2-pyridylmethyl)ethane-1,2diamine; 1,2-bis(o-aminophenoxy)ethane-N,N,N',N'-tetraacetic acid; N-(2-Hydroxyethyl)ethylenediamine-N,N',N'-triacetic acid; and salts thereof.

Embodiment G is composition of any one of the preceding Embodiments, further comprising ferric iron.

Embodiment H is the composition of Embodiment G, wherein the ferric iron comprises dissolved ferric iron ions.

Embodiment I is the composition of Embodiment G or Embodiment H, wherein the ferric iron is present at a concentration of about 50 μM to about 350 μM.

Embodiment J is the composition of any one of Embodiments G through I, wherein the organic iron-chelating reagent comprises EGTA, wherein a molar ratio of the ferric iron to the EGTA is about 0.04 to about 0.28.

Embodiment K is the composition of any one of the preceding Embodiments, further comprising a nanoparticle dispersion stabilizer.

Embodiment L is the composition of Embodiment K, wherein the nanoparticle dispersion stabilizer comprises 2-hydroxypropane-1,2,3-tricarboxylic acid or a salt thereof.

Embodiment M is the composition of Embodiment K or Embodiment L, wherein the organic iron-chelating reagent and the nanoparticle dispersion stabilizer are distinct molecules.

Embodiment N is the composition of any one of the preceding Embodiments, wherein the non-ionic surfactant has a Hydrophilic-lipophilic balance of about 11 to about 16.

Embodiment O is the composition of any one of the preceding Embodiments, wherein the nonionic surfactant is selected from the group consisting of t-octylphenoxypolyethoxyethanol, sorbitan fatty acid ester, polyoxyethylene sorbitan fatty acid ester, polyoxyethylene alkyl ether, nonylphenol, lauryl alcohol, polyethylene glycol, polyoxyethylene•polyoxypropylene block polymer, polyoxyethylene alkyl amine, and polyoxyethylene fatty acid bisphenyl ether.

Embodiment P is the composition of any one of Embodiments B through M, wherein the non-ionic surfactant is present at a concentration up to about 0.3% (mass/volume).

Embodiment Q is the composition of Embodiment N, wherein the non-ionic surfactant is present at a concentration of 0.005% to 0.05% w/v.

Embodiment R is the composition of any one of the preceding Embodiments, further comprising polyvinylpyrrolidone.

Embodiment S is the composition of Embodiment R, wherein the polyvinylpyrrolidone is present at a concentration of up to 0.043% w/v.

Embodiment T is the composition of any one of the preceding Embodiments, wherein the composition further comprises fluorosurfactant.

Embodiment U the composition of Embodiment of T, wherein fluorosurfactant is FC-4430™.

Embodiment V is the composition of any one of the preceding Embodiments, wherein the composition further comprises an indicator dye.

Embodiment W is the composition of Embodiment of V, wherein indicator dye is cresol red.

Embodiment X is the composition of any one of the preceding Embodiments, wherein the composition further comprises an effective amount of a preservative.

Embodiment Y is the composition of Embodiment of X wherein preservative is methylisothiazolinone.

Embodiment Z is the composition of any one of the preceding Embodiments, further comprising an effective amount of non-fat milk.

Embodiment AA is the composition of any one of the preceding Embodiments, for use in detecting microorganism in a sample.

Embodiment AB is the composition of any one of the preceding Embodiments, wherein the sample is a food sample, clinical sample or a culture broth.

Embodiment AC is the composition of Embodiment of AB, wherein food sample comprises protein.

Embodiment AD is the composition of Embodiment AC, wherein protein is ferritin.

Embodiment AE is the composition of any one of the preceding Embodiments, wherein the sample comprises a culture broth.

Embodiment AF is the composition of Embodiment AE, wherein the sample comprises esculin.

Embodiment AG is a nucleic acid amplification method, the method comprising:

a) contacting a composition comprising a plurality of zirconium oxide particles, a non-ionic surfactant and a monovalent salt of ethylene glycol tetraacetic acid (EGTA) with a target sample to form an aqueous mixture, wherein the composition has a pH of about 8.45 to 8.85;

b) subjecting the aqueous mixture of step a) to a thermal lysis process; and c) after step b), subjecting a portion of the aqueous mixture to a nucleic acid amplification process.

Embodiment AH is the method of Embodiment AG, wherein the plurality of zirconium oxide particles has a surface area of about 10 $m^2$/L to about 600 $m^2$/L Embodiment AI is the method of Embodiment AG or Embodiment AH, for eliminating inhibition of nucleic acid amplification caused by interfering components present in the sample.

Embodiment AJ is the method of any one of Embodiments AG though AI, wherein the nucleic acid amplification method comprises loop-mediated isothermal amplification.

Embodiment AK is the method of any one of the Embodiments AG through AI, wherein the nucleic acid amplification method comprises a thermocycling polymerase chain reaction process.

Embodiment AL is the method of any one of Embodiments AG through AK, wherein the composition comprises water.

Embodiment AM is the method of any one of the Embodiments AG to AL, wherein the sample is a food sample, clinical sample or a culture broth.

Embodiment AN is the method of any one of the Embodiment AG to AM, wherein food sample comprises protein.

Embodiment AO is the method of Embodiment AN, wherein protein is ferritin.

Embodiment AP is the method of any one of the Embodiments AG through AO, wherein the sample is culture broth.

Embodiment AQ is the method of Embodiment AP, wherein the sample comprises esculin.

Embodiment AR is the method of any one of the Embodiments AG through AQ, wherein the sample is incubated in a culture broth at about 41.5° C. prior to step a).

Embodiment AS is the method of any one of Embodiments AG through AR, wherein composition further comprises a buffering agent, and an enhancer for facilitating LAMP-BART nucleic acid amplification reaction or an enhancer for facilitating a qPCR reaction.

Embodiment AT is the method of Embodiment AS, wherein the enhancer is selected from the group consisting of potassium chloride, ammonium sulfate, magnesium sulfate heptahydrate and combinations thereof.

Embodiment AU is the method of Embodiment AS, wherein the buffering agent comprises Tris base.

Embodiment AV is the method of any one of the Embodiments AG through AU, wherein the subjecting the mixture to a thermal lysis process comprises heating the mixture to about 100° C. for about 15 minutes and subsequently cooling the mixture to about 40° C. for about 5 minutes.

Embodiment AW is the method of Embodiment AV, wherein, after cooling the mixture to about 40° C., the method further comprises contacting the mixture with a reagents for LAMP-BART isothermal amplification.

Embodiment AX is the method of any one of Embodiments AG through AW, wherein subjecting a portion of the aqueous mixture to a nucleic acid amplification process comprises amplifying a target polynucleotide associated with a pathogenic microorganism.

Embodiment AY is the method of Embodiment AX, wherein amplifying a target polynucleotide associated with a pathogenic microorganism comprises amplifying a target polynucleotide associated with a pathogenic microorganism selected from the group consisting of a *Salmonella* species, a *Clostridium* species, *Bacillus cereus*, a *Campylobacter* species, a *Staphylococcus* species, *Escherichia coli*, a *Listeria* species, a *Vibrio* species, and a *Yersinia* species.

Embodiment AZ is a kit, comprising:

a plurality of zirconium oxide particles;

a non-ionic surfactant; and an organic iron-chelating reagent;

wherein the organic iron-chelating reagent has a first affinity constant greater than or equal to $10^{4.2}$ with respect to ferric iron and a second affinity constant less than $10^{3.8}$ with respect to magnesium, wherein the first affinity constant and the second affinity constant are determined in 20° C. deionized water at pH 8.45.

Embodiment BA is the kit of Embodiment AZ, wherein the plurality of particles has a mean particle size that is less than about 1 μm.

Embodiment BB is the kit of Embodiment AZ or Embodiment BA, wherein the organic iron-chelating reagent comprises a plurality of carboxylate groups.

Embodiment BC is the kit of any one of Embodiment AZ through BB, wherein the organic iron-chelating reagent is selected from the group consisting of ethylene glycol-bis(2-aminoethylether)-N,N,N',N'-tetraacetic acid; N,N,N',N'-tetrakis(2-pyridylmethyl)ethane-1,2-diamine; 1,2-bis(o-aminophenoxy)ethane-N,N,N',N'-tetraacetic acid; N-(2-Hydroxyethyl)ethylenediamine-N,N',N'-triacetic acid; and salts thereof.

Embodiment BD is the kit of any one of Embodiments AZ through BC, further comprising ferric iron.

Embodiment BE is the kit of Embodiment BD, wherein the ferric iron is present in the kit as ferric ammonium citrate.

Embodiment BF is the kit of any one of Embodiments AZ through BE, further comprising a nanoparticle dispersion stabilizer.

Embodiment BG is the kit of Embodiment BF, wherein the nanoparticle dispersion stabilizer comprises 2-hydroxypropane-1,2,3-tricarboxylic acid or a salt thereof.

Embodiment BH is the kit of Embodiment BF or Embodiment BG, wherein the organic iron-chelating reagent and the nanoparticle dispersion stabliizer are distinct molecules.

Embodiment BI is the kit of any one of Embodiments AZ through BH, wherein the non-ionic surfactant has a Hydrophilic-lipophilic balance of about 11 to about 16.

Embodiment BJ is the kit of any one of Embodiments AZ through BI, wherein the nonionic surfactant is selected from the group consisting of t-octylphenoxypolyethoxyethanol, sorbitan fatty acid ester, polyoxyethylene sorbitan fatty acid ester, polyoxyethylene alkyl ether, nonylphenol, lauryl alcohol, polyethylene glycol, polyoxyethylene.polyoxypropylene block polymer, polyoxyethylene alkyl amine, and polyoxyethylene fatty acid bisphenyl ether.

Embodiment BK is the kit of any one of Embodiments AZ through BJ, further comprising polyvinylpyrrolidone.

Embodiment BL is the kit of any one of the Embodiments AZ through BK, wherein the kit further comprises a fluorosurfactant.

Embodiment BM is the kit of Embodiment BL, wherein fluorosurfactant is FC-4430™.

Embodiment BN is the kit of any one of Embodiments AZ through BM, wherein the kit further comprises an indicator dye.

Embodiment BO is the kit of Embodiment BN, wherein the indicator dye is cresol red.

Embodiment BP is the kit of any one of the Embodiments AZ through BO, wherein the kit further comprises a preservative.

Embodiment BQ is the kit of Embodiment BP, wherein the preservative is methylisothiazolinone.

Embodiment BR is the kit of any one of the Embodiments AZ through BQ, wherein the kit further comprises a buffering agent.

Embodiment BS is the kit of any one of the Embodiments AZ through BR, wherein the kit further comprises a buffering agent, an enhancer for facilitating LAMP-BART reaction or a qPCR reaction, and a combination of any two or more of the foregoing components.

Embodiment BT is the kit of Embodiment BS, wherein the enhancer is selected from the group consisting of potassium chloride, ammonium sulfate, magnesium sulfate heptahydrate and combinations thereof.

Embodiment BU is the kit of Embodiment BS, wherein the buffering agent comprises Tris base.

Embodiment BV is the kit of any one of Embodiments AZ through BU, further comprising an effective amount of non-fat milk.

Embodiment BW is the kit of any one of the Embodiments AZ through BV, wherein at least one of ferric ammonium citrate, polyvinylpyrrolidone, a non-ionic surfactant and a monovalent salt of ethylene glycol tetraacetic acid is disposed in an aqueous medium.

Embodiment BX is the kit of Embodiment BW, wherein the aqueous medium has a pH of about 8.45 to 8.85.

Embodiment BY is the kit of any one of the Embodiments AZ through BX, wherein the kit further comprises a reagent for amplifying a target polynucleotide.

Embodiment BZ is the kit of Embodiment BY, wherein the target polynucleotide is associated with a pathogenic microorganism.

Embodiment CA is the kit of Embodiment BZ, wherein the pathogenic microorganisms is selected from the group consisting of a *Salmonella* species, a *Clostridium* species, *Bacillus cereus*, a *Campylobacter* species, a *Staphylococcus* species, *Escherichia coli*, a *Listeria* species, a *Vibrio* species, and a *Yersinia* species.

Embodiment CB is the kit of any one of the Embodiments AZ through CA, wherein the kit comprises instructions for use.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is distilled water, and all molecular weights are weight average molecular weight.

Examples 1-8

Compositions Comprising Ferric Ions and Various Quantities of Zirconium Oxide Particles A zirconium oxide nanoparticle dispersion (10% w/w in water; ≤100 nm mean particle size (BET); surface area 11 $m^2/mL$; Part No. 643025) was obtained from Sigma Chemical Co. The test compositions were prepared with each component added to deionized water in the order specified in Table 1. Comparative Example 1 was prepared as described for Example 1 with the exception that no zirconium oxide particles and no potassium citrate was added to the composition. Each composition of Examples 1-8 and Comparative Example 1 included 200 mg/L ferric ammonium citrate and 320 mg/L TRITON X-100. The amounts of potassium citrate and zirconium oxide dispersion used in each Example and in Comparative Example 1 are shown in Table 2.

TABLE 1

Test compositions for Examples 1-8 and Comparative Example 1. The order of addition of each component of the composition is also shown.

| Order of Addition to Water | Component | Concentration |
|---|---|---|
| 1 | Ferric ammonium citrate | 200 mg/L |
| 2 | Potassium Citrate | 0, 120, 180, or 240 mg/L |
| 3 | TRITON X-100 | 320 mg/L |
| 4 | PVP | 430 mg/L |
| 5 | Zirconium oxide dispersion (10% w/w) | 0-600 $m^2/L$ |
| 6 | Cresol Red | 10 mg/L |
| 7 | Magnesium sulfate heptahydrate | 73.8 mg/L |
| 8 | Potassium chloride | 3.19 g/L |
| 9 | Tris base | 2.72 g/L |
| 10 | Ammonium sulfate | 1.41 g/L |
| 11 | EGTA | 475 mg/L |
| 12 | Proclin ® 950 (9.5%) | 0.526 mL/L |

TABLE 2

Amounts of ferric ammonium citrate, TRITON X-100, zirconium oxide particle dispersion, and additional citrate stabilizer added to each composition of Examples 1-8.

| | Potassium Citrate (mg/L) | $ZrO_2$ Dispersion ($m^2/L$) |
|---|---|---|
| Comparative Example 1 | 0 | 0 |
| Example 1 | 0 | 10 |
| Example 2 | 0 | 25 |
| Example 3 | 120 | 50 |
| Example 4 | 120 | 100 |
| Example 5 | 180 | 200 |

TABLE 2-continued

Amounts of ferric ammonium citrate, TRITON X-100, zirconium oxide particle dispersion, and additional citrate stabilizer added to each composition of Examples 1-8.

|  | Potassium Citrate (mg/L) | $ZrO_2$ Dispersion $(m^2/L)$ |
|---|---|---|
| Example 6 | 180 | 300 |
| Example 7 | 240 | 400 |
| Example 8 | 240 | 600 |

Effect of Zirconium Oxide Particle Surface Area in Compositions Comprising Ferric Ions on the Removal of Inhibitory Substances from a Nucleic Acid Amplification Reaction.

Lysozyme is a protein (enzyme) that is known to inhibit LAMP-BART nucleic acid amplification and/or detection reactions. Lysozyme (Part No. L3790) was obtained from Sigma Chemical Co. (St. Louis, Mo.). Samples were prepared with lysozyme dissolved in buffered peptone water at a lysozyme concentration of 2.5 mg/mL. Twenty-microliter aliquots of the lysozyme solutions were added to 580 microliters of the test compositions described above (Table 2) in a Neptune (2600.X) lysis tube (Biotix, Inc. San Diego, Calif. 92121).

Each tube containing the mixture of lysozyme and respective test composition was heated in a 100° C. heat block for 15 minutes, cooled to ~40° C. and then a 20 μL aliquot of the mixture was added to a reaction tube containing a generic matrix control LAMP-BART pellet (Part No. MDMC96NA, available from 3M Company; St. Paul, Minn.). After dissolving the pellet, the reaction tube was placed in a MDS instrument (Part No. MDS 100; available from 3M Company; St. Paul, Minn.) and bioluminescence (i.e., the BART reaction) was recorded for 75 minutes. The Time-To-Positive (TTP) for the BART reaction was recorded and is shown in Table 3 (n=3).

TABLE 3

Average time-to-positive (TTP) for a LAMP-BART nucleic acid amplification reaction using a generic reaction control.

|  | TTP (min.) | Ave. TTP (min.) |
|---|---|---|
| Comparative Example 1 | 38 | 44 |
| " | 49 |  |
| " | 45 |  |
| Example 1 | 42 | 38 |
| " | 38 |  |
| " | 35 |  |
| Example 2 | 36 | 32 |
| " | 31 |  |
| " | 30 |  |
| Example 3 | 15 | 16 |
| " | 16 |  |
| " | 16 |  |
| Example 4 | 16 | 16 |
| " | 16 |  |
| " | 16 |  |
| Example 5 | 15 | 16 |
| " | 16 |  |
| " | 16 |  |
| Example 6 | 16 | 16 |
| " | 16 |  |
| " | 16 |  |
| Example 7 | 16 | 16 |
| " | 16 |  |
| " | 16 |  |
| Example 8 | 26 | 19 |
| " | 16 |  |
| " | 16 |  |

The data in Table 3 indicate that the presence of zirconium oxide particles decreases the TTP (i.e., the minimum time needed for detection of amplified nucleic acid) by decreasing known the inhibitory effect of the lysozyme. The data further indicate a dose-dependent effect of the particles, where increasing the apparent surface area of the particles up to about 50 $m^2/L$ leads to lower TTPs. Light intensity was measured in terms of the Relative Light Units (RLU) which is directly proportional to the nucleic acid amplification.

Examples 9-14

Compositions Comprising Zirconium Oxide Particles and Various Concentrations of Surfactant and Ferric Ions Test compositions were prepared with the components and their respective order of addition to deionized water shown in Table 4. In these Examples, the ferric iron ion and nonionic surfactant concentrations were varied according to Table 5. The zirconium oxide surface area was held constant at 20 $m^2/L$. Samples (600 μL) were prepared as described for Example 1 and Comparative Examples 2-7. Aliquots (20 μL) of the lysozyme solution were added to 580 microliters of the test compositions in a Neptune (2600.X) lysis tube.

TABLE 4

Test compositions for Examples 9-14 and Comparative Examples 2-7. The order of addition of each component of the composition is shown.

| Order of Addition to Water | Component | Concentration |
|---|---|---|
| 1 | Ferric ammonium citrate | 0 or 200 mg/L |
| 2 | TRITON X-100 | 100-320 mg/L |
| 3 | PVP | 430 mg/L |
| 4 | Zirconium oxide dispersion | 0 or 20 $m^2/L$ |
| 5 | Cresol Red | 10 mg/L |
| 6 | Magnesium sulfate heptahydrate | 73.8 mg/L |
| 7 | Potassium chloride | 3.19 g/L |
| 8 | Tris base | 2.72 g/L |
| 9 | Ammonium sulfate | 1.41 g/L |
| 10 | EGTA | 475 mg/L |
| 11 | Proclin ® 950 (9.5%) | 0.526 mL/L |

TABLE 5

Amounts of ferric ammonium citrate, TRITON X-100, and zirconium oxide particle dispersion added to each composition of Examples 9-14 and Comparative Examples 2-7.

|  | Ferric Ammonium Citrate (mg/L) | TRITON X-100 (mg/L) | $ZrO_2$ Dispersion $(m^2/L)$ |
|---|---|---|---|
| Comparative Example 2 | 0 | 100 | 0 |
| Comparative Example 3 | 0 | 250 | 0 |
| Comparative Example 4 | 0 | 320 | 0 |
| Comparative Example 5 | 200 | 100 | 0 |
| Comparative Example 6 | 200 | 250 | 0 |
| Comparative Example 7 | 200 | 320 | 0 |
| Example 9 | 0 | 100 | 20 |
| Example 10 | 0 | 200 | 20 |
| Example 11 | 0 | 320 | 20 |
| Example 12 | 200 | 100 | 20 |
| Example 13 | 200 | 250 | 20 |
| Example 14 | 200 | 320 | 20 |

Example 15

Effect of Surfactant and Ferric Iron Ion Concentrations in Compositions Comprising Zirconium Oxide Particles on the Removal of Inhibitory Substances from an Isothermal Nucleic Acid Amplification Reaction Raw, pieces and parts of a chicken naturally contaminated with *Camplyobacter* strains were stomached in Whirl-Pak stomacher bag (part number: B01195WA) for 2 minutes at 230 rpm at an enrichment ratio of 1 g per 9 mL of Bolton broth with laked horse blood. This stomached sample was incubated at 41.5° C. for 24 hours. For positive samples, 20 µL of these enriched samples were added to 580 uL of the lysis compositions described in Table 5 (using a Neptune (2600.X) lysis tube.) Each tube was heated in a 100° C. heat block for 15 minutes, cooled to ~40° C., and a 20 µL aliquot of the mixture was then added to a reaction tube containing a trehalose-stabilized freeze dried *Campylobacter* LAMP-BART pellet that contained the ingredients shown in Table 6.

TABLE 6

Ingredients used in the *Campylobacter* LAMP-BART pellet that was hydrated with 20 microliters of lysate mixture.

| Component | Amount |
|---|---|
| Potassium acetate | 22.5 nmoles |
| Magnesium sulfate | 30 nmoles |
| Dithiothreitol | 150 nmoles |
| Luciferin | 1.5 µg |
| Adenosine-5'-O-phosphosulfate (APS) | 3.75 µmoles |
| Ultra-Glo Luciferase | 84 ng |
| ATP sulfurylase | 5.6 mU |
| d-NTP mix | 6 µmoles (each dNTP) |
| Bst 2.0 DNA polymerase | 1.2 U |
| *Campylobacter* LAMP Forward Primer (SEQ ID NO: 1) | 12 fmoles |
| *Campylobacter* LAMP Backward Primer (SEQ ID NO: 2) | 12 fmoles |
| Loop Forward Primer (SEQ ID NO: 3) | 6 fmoles |
| Loop Backward Primer (SEQ ID NO: 4) | 6 fmoles |
| Displacer Forward Primer (SEQ ID NO: 5) | 3 fmoles |
| Displacer Backward Primer (SEQ ID NO: 6) | 3 fmoles |

(SEQ ID NO: 1)-GGGCTTTTCAACGCCTATGCGAAGTGATCTATCCATGAGCAA
(SEQ ID NO: 2)-TCGTGATAGCTGGTTCTCTCCGCCATTCAGTGCTCTACCCCCTTAT
(SEQ ID NO: 3)-TCTTACACTAGCTTCAACT
(SEQ ID NO: 4)-ATATTTAGGTATAGCGTTGTGTC
(SEQ ID NO: 5)-GCTTAGTCAGATGCTGCAGAC
(SEQ ID NO: 6)-GCCGCCTGACTGCTGTG

After dissolving the pellet, the reaction tube was placed in a MDS instrument as described for Example 1 and bioluminescence (i.e., the BART reaction) was recorded for 75 minutes. The Time-To-Positive (TTP) for the BART reaction was recorded and is shown in Table 7 for Examples 9-14 and Comparative Examples 2-7 (n=3).

Example 16

Effect of Surfactant and Ferric Iron Ion Concentrations in Compositions Comprising Zirconium Oxide Particles on the Removal of Inhibitory Substances from a Thermocycling Nucleic Acid Amplification Reaction A five microliter aliquot of each mixture described in Example 15 was added to a qPCR master mixture consisting of PCR buffer, 0.2 mM dNTP's, 3 mM MgCl2, 2.5 U of Taq DNA polymerase, 0.625 µM forward primer [SEQ ID NO: 7 (CTGCTTAACACAAGTTGAGTAGG)], 0.625 µM reverse primer [SEQ ID NO: 8 (TTCCTTAGGTAC-CGTCAGAA)], Brilliant III Master Mix (Agilent Technologies), and 0.156 µM *Campylobacter* probe [SEQ ID NO: 9 (FAM-TGTCATCCTCCACGCGGCGTTGCTGC-TAMRA)]. Note—each of the aforementioned concentrations are reported as final concentrations after addition of the lysis mixture.

Thermocycling reactions were run for 40 cycles using the following protocol: (1) denature (95° C. for 30 seconds), (2) anneal (58° C. for 30 seconds), and (3) extend (72° C. for 60 seconds). All thermocycling reactions were run in an Agilent Stratagene 3005P thermocycler. The Ct Values for Examples 9-14 and Comparative Examples 2-7 are provided in Table 7 (n=3).

TABLE 7

Average time-to-positive (TTP) for the LAMP-BART
Campylobacter-amplification reactions and qPCR Ct values
for the thermocycling Campylobacter-amplification reactions.

| Composition | LAMP-BART TTP (min) | $C_t$ Value for qPCR |
|---|---|---|
| Comparative Example 2 | 75 | 37.94 |
| Comparative Example 2 | 75 | 33.76 |
| Comparative Example 2 | 75 | 34.95 |
| Comparative Example 3 | 56.25 | 32.42 |
| Comparative Example 3 | 58.25 | 35 |
| Comparative Example 3 | 70 | 38 |
| Comparative Example 4 | 70 | 39 |
| Comparative Example 4 | 75 | 38.97 |
| Comparative Example 4 | 75 | 35.98 |
| Comparative Example 5 | 30.5 | 31.88 |
| Comparative Example 5 | 30.5 | 31.51 |
| Comparative Example 5 | 28 | 31.84 |
| Comparative Example 6 | 70 | 34.05 |
| Comparative Example 6 | 59.25 | 35.26 |
| Comparative Example 6 | 56 | 34.22 |
| Comparative Example 7 | 75 | 34.4 |
| Comparative Example 7 | 43.25 | 36.1 |
| Comparative Example 7 | 47 | 34.97 |
| Example 9 | 24.75 | 33.02 |
| " | 26.5 | 31.42 |
| " | 25.5 | 33.32 |
| Example 10 | 26.5 | 37.05 |
| " | 27.75 | 32.51 |
| " | 27.25 | 32.91 |
| Example 11 | 25.75 | 33.11 |
| " | 29.75 | 32.67 |
| " | 25.25 | 32.51 |
| Example 12 | 19.75 | 27.93 |
| " | 20 | 27.88 |
| " | 19 | 27.65 |
| Example 13 | 20.25 | 27.87 |
| " | 21.5 | 27.95 |
| " | 20.25 | 27.77 |
| Example 14 | 19.5 | 27.5 |
| " | 21.5 | 27.48 |
| " | 20.25 | 27.49 |

The data show that addition of ferric ions or nonionic surfactant to the composition improved the amplification reaction relative to control reactions that did not contain them. In addition, the data show that the combination of zirconium particles, nonionic surfactant, and ferric ions significantly improved the amplification reaction as measured by LAMP-BART time-to-positive results and qPCR Ct values.

Use of Zirconium Oxide Particles to Remove Inhibitory Materials for Spice Samples Subjected to LAMP-BART Nucleic Acid Amplification Procedure.

Five different samples of spices were prepared with two different enrichment schemes. In the first scheme 5 grams of the spice were added to 95 mL of buffered peptone water in a whirl-pak stomacher bag, and stomached for 2 minutes at 230 rpm. In the second scheme 5 grams of the spice were added to 95 mL of buffered peptone water supplemented with non-fat dry milk at a concentration of 50 g/L in a whirl-pak stomacher bag, and stomached for 2 minutes at 230 rpm. Samples were incubated for 24 hours at 37° C. After the incubation period, 20 µL of each sample were added to individual tubes containing 580 uL of the lysis composition described in example 14. The resulting mixtures were heated in a 100° C. heat block for 15 minutes, cooled to ~40° C. and a 20 µL aliquot of each mixture was then added to an individual reaction tube containing a 3M MDs Matrix Control Pellet (cat # MDMC96NA). Each tube was processed for LAMP-BART amplification as described in Examples 1-8. The TTP for each reaction is listed in Table 8

TABLE 8

| Spice Sample | TTP (min) (BPW with Non-fat dry milk) | TTP (min) (BPW only) |
|---|---|---|
| Allspice | 16.3 | 39.5 |
| Basil | 18.3 | 75 |
| Instant Coffee | 22.3 | 75 |
| Marjoram | 23.3 | 75 |
| Thyme | 21.5 | 75 |

The present disclosure, in general, is suitable for use in both research and diagnostics. That is, the compositions, methods and kits of the present disclosure may be used for the purpose of identifying various nucleic acids or expressed genes, or for other research purposes. Likewise, the compositions, methods and kits can be used to diagnose numerous diseases or disorders of humans and animals. In addition, they can be used to identify diseased or otherwise tainted food products (e.g., foods that are infected with one or more pathogenic organisms/micro-organisms), or the presence of toxic substances or toxin-producing organisms in a sample. Thus, the compositions and methods have human health and veterinary applications, as well as food testing and homeland security applications.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:

1. An aqueous composition for eliminating sample inhibition in a nucleic acid amplification reaction, said aqueous composition comprising:
   a plurality of zirconium oxide particles;
   a non-ionic surfactant at a concentration greater than or equal to 0.005% (mass/volume); and
   an organic iron-chelating reagent;
   wherein the composition has a pH of about 8.45 to 8.85;
   wherein the organic iron-chelating reagent has a first affinity constant greater than or equal to $10^{4.2}$ with respect to ferric iron and a second affinity constant less than $10^{3.8}$ with respect to magnesium, wherein the first affinity constant and the second affinity constant are determined in 20° C. deionized water at pH 8.45;
   and wherein the composition further comprises a nanoparticle dispersion stabilizer, polyvinylpyrrolidone, or both a nanoparticle dispersion stabilizer and polyvinylpyrrolidone.

2. The aqueous composition of claim 1, wherein the plurality of particles has a mean particle size that is less than or equal to 100 nm.

3. The aqueous composition of claim 1, wherein the organic iron-chelating reagent comprises a plurality of carboxylate groups.

4. The aqueous composition of claim 1, further comprising ferric iron.

5. The aqueous composition of claim 1, further comprising a nanoparticle dispersion stabilizer.

6. The aqueous composition of claim 1, wherein the non-ionic surfactant has a Hydrophilic-lipophilic balance of about 11 to about 16.

7. The aqueous composition of claim 1, further comprising polyvinylpyrrolidone.

8. The aqueous composition of claim 1, further comprising an indicator dye.

9. A nucleic acid amplification method, said method comprising:
   a) contacting a composition of claim 1;
   b) subjecting the aqueous mixture of step a) to a thermal lysis process; and
   c) after step b), subjecting a portion of the aqueous mixture to a nucleic acid amplification process.

10. The method of claim 9, wherein the sample is incubated in a culture broth prior to step a).

11. The method of claim 9, wherein the composition further comprises a buffering agent, an enhancer for facilitating a LAMP-BART nucleic acid amplification reaction or an enhancer for facilitating a qPCR reaction.

12. The method of claim 9, wherein subjecting the mixture to thermal lysis comprises heating the mixture to about 100° C. for about 15 minutes.

13. A kit, comprising:
   a plurality of zirconium oxide particles;
   a non-ionic surfactant; and
   an organic iron-chelating reagent;
   wherein the organic iron-chelating reagent has a first affinity constant greater than or equal to $10^{4.2}$ with respect to ferric iron and a second affinity constant less than $10^{3.8}$ with respect to magnesium, wherein the first affinity constant and the second affinity constant are determined in 20° C. deionized water at pH 8.45; and
   a nanoparticle dispersion stabilizer, polyvinylpyrrolidone, or both a nanoparticle dispersion stabilizer and polyvinylpyrrolidone.

14. The kit of claim 13, wherein the organic iron-chelating reagent comprises a plurality of carboxylate groups.

15. The kit of claim 13, further comprising ferric iron.

16. The kit of claim 13, further comprising a nanoparticle dispersion stabilizer.

17. The kit of claim 13, wherein the non-ionic surfactant has a Hydrophilic-lipophilic balance of about 11 to about 16.

18. The kit of claim 13, further comprising polyvinylpyrrolidone.

19. The kit of claim 13, further comprising a component selected from the group consisting of a fluorosurfactant, an indicator dye, a preservative, a buffering agent, an enhancer of a LAMP-BART reaction or a qPCR reaction, and a combination of any two or more of the foregoing components.

20. The kit of claim 13, wherein any one or more of the zirconium particles, the ferric iron, the polyvinylpyrrolidone, the non-ionic surfactant, the fluorosurfactant, the indicator dye, the preservative, the buffering agent, or the enhancer is disposed in an aqueous solution, wherein the aqueous solution has a pH of about 8.45 to 8.85.

* * * * *

```
                           SEQUENCE LISTING

<160> NUMBER OF SEQ ID NOS: 9

<210> SEQ ID NO 1
<211> LENGTH: 42
<212> TYPE: DNA
<213> ORGANISM: Campylobacter jejuni

<400> SEQUENCE: 1
gggcttttca acgcctatgc gaagtgatct atccatgagc aa                          42

<210> SEQ ID NO 2
<211> LENGTH: 46
<212> TYPE: DNA
<213> ORGANISM: Campylobacter jejuni

<400> SEQUENCE: 2
tcgtgatagc tggttctctc cgccattcag tgctctaccc ccttat                      46

<210> SEQ ID NO 3
<211> LENGTH: 19
<212> TYPE: DNA
<213> ORGANISM: Artificial Sequence
<220> FEATURE:
<223> OTHER INFORMATION: Loop Forward Primer for LAMP amplification

<400> SEQUENCE: 3
tcttacacta gcttcaact                                                    19

<210> SEQ ID NO 4
<211> LENGTH: 23
<212> TYPE: DNA
<213> ORGANISM: Artificial Sequence
<220> FEATURE:
<223> OTHER INFORMATION: Loop Backward for LAMP amplification

<400> SEQUENCE: 4
atatttaggt atagcgttgt gtc                                               23

<210> SEQ ID NO 5
<211> LENGTH: 21
<212> TYPE: DNA
<213> ORGANISM: Artificial Sequence
<220> FEATURE:
<223> OTHER INFORMATION: Displacer Forward Primer for LAMP amplification

<400> SEQUENCE: 5
gcttagtcag atgctgcaga c                                                 21

<210> SEQ ID NO 6
<211> LENGTH: 17
<212> TYPE: DNA
<213> ORGANISM: Artificial Sequence
<220> FEATURE:
<223> OTHER INFORMATION: Displacer Backward Primer for LAMP
      amplification

<400> SEQUENCE: 6
gccgcctgac tgctgtg                                                      17

<210> SEQ ID NO 7
```

```
<211> LENGTH: 23
<212> TYPE: DNA
<213> ORGANISM: Campylobacter jejuni

<400> SEQUENCE: 7
ctgcttaaca caagttgagt agg                                        23

<210> SEQ ID NO 8
<211> LENGTH: 20
<212> TYPE: DNA
<213> ORGANISM: Campylobacter jejuni

<400> SEQUENCE: 8
ttccttaggt accgtcagaa                                            20

<210> SEQ ID NO 9
<211> LENGTH: 26
<212> TYPE: DNA
<213> ORGANISM: Campylobacter jejuni

<400> SEQUENCE: 9
tgtcatcctc cacgcggcgt tgctgc                                     26
```